US011858892B2

United States Patent
Xu et al.

(10) Patent No.: US 11,858,892 B2
(45) Date of Patent: Jan. 2, 2024

(54) ADSORBENT FOR REMOVING METHANOL OR $CO_2$ FROM A HYDROCARBON STREAM

(71) Applicant: UOP LLC, Des Plaines, IL (US)

(72) Inventors: Qing Xu, Shanghai (CN); Zhe Lin, Shanhai (CN); Lu Wang, Shanghai (CN)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/935,254

(22) Filed: Sep. 26, 2022

(65) Prior Publication Data
US 2023/0212096 A1    Jul. 6, 2023

Related U.S. Application Data

(60) Provisional application No. 63/266,290, filed on Dec. 31, 2021.

(51) Int. Cl.
*C07C 7/12* (2006.01)
*B01D 53/02* (2006.01)
(Continued)

(52) U.S. Cl.
CPC ............ *C07C 7/12* (2013.01); *B01D 53/02* (2013.01); *B01J 20/183* (2013.01); *B01J 20/2803* (2013.01); *B01D 2253/108* (2013.01); *B01D 2256/24* (2013.01); *B01D 2257/504* (2013.01); *B01D 2257/70* (2013.01)

(58) Field of Classification Search
CPC .......... C07C 7/12; B01D 53/02; B01D 53/04; B01D 2253/108; B01D 2256/24; B01D 2257/504; B01D 2257/70; B01J 20/183; B01J 20/2803
See application file for complete search history.

(56) References Cited

U.S. PATENT DOCUMENTS 2,882,243 A * 4/1959 Milton ................ B01J 20/18
                                                        208/2
4,371,718 A   2/1983 Hutson, Jr.
(Continued)

FOREIGN PATENT DOCUMENTS

CN    105582885 A    5/2016
CN    105585405 A    5/2016

OTHER PUBLICATIONS

International Search Report from corresponding PCT application No. PCT/US2022/082412, dated May 1, 2023.
(Continued)

*Primary Examiner* — In Suk C Bullock
*Assistant Examiner* — Jason Y Chong

(57) ABSTRACT

A process of removing methanol, $CO_2$, or both from a hydrocarbon stream is described. The process uses an adsorbent comprising binderless type 3A zeolite. The adsorbent has high methanol removal capacity and low olefin co-adsorption capacity, as well as low reactivity in an olefin stream. This allows reduced adsorbent loading while maintaining downstream catalyst performance and product quality. The adsorbent comprises a type 3A zeolite comprising less than 5% of a binder and an ion exchange ratio of 30% to 70%. The adsorption process can obtain an outlet methanol content of 1 ppmw or less.

18 Claims, 2 Drawing Sheets

(51) Int. Cl.
*B01J 20/18* (2006.01)
*B01J 20/28* (2006.01)

(56) References Cited

U.S. PATENT DOCUMENTS

| | | | |
|---|---|---|---|
| 4,424,144 A | | 1/1984 | Pryor et al. |
| 5,041,402 A | * | 8/1991 | Casci .................... C10G 45/64 |
| | | | 502/67 |
| 2011/0027156 A1 | * | 2/2011 | Eisinger .................. B01J 20/10 |
| | | | 422/187 |
| 2014/0217324 A1 | | 8/2014 | Weston et al. |
| 2014/0364672 A1 | | 12/2014 | Bracco et al. |
| 2016/0367948 A1 | | 12/2016 | Song et al. |
| 2018/0015407 A1 | | 1/2018 | Vittenet et al. |
| 2018/0056235 A1 | * | 3/2018 | Wang ................... B01D 53/261 |
| 2019/0119182 A1 | | 4/2019 | McCormick et al. |

OTHER PUBLICATIONS

Written Opinion from from corresponding PCT application No. PCT/US2022/082412, completed May 1, 2023.

* cited by examiner

ADSORBENT FOR REMOVING METHANOL OR CO₂ FROM A HYDROCARBON STREAM

RELATED APPLICATIONS

This application claims priority to U.S. Provisional Patent Application Ser. No. 63/266,290, filed on Dec. 31, 2021, the entirety of which is incorporated herein by reference.

BACKGROUND

The presence of methanol and/or $CO_2$ in certain hydrocarbon streams can cause problems with downstream reactions. For example, methanol can react with the catalyst in a downstream process, degrading catalyst performance. $CO_2$ can cause equipment blocking and a decrease in catalyst performance. As a result, methanol must be removed from the hydrocarbon stream to a concentration of less than 1 ppmw in some processes, for example.

Various technologies have been used to remove methanol from hydrocarbon streams such as olefins. U.S. Pat. No. 4,371,718 describes the use of activated alumina to remove methanol from a hydrocarbon stream. CN 105582885 and CN 105585405 describe the use of an MFI/FAU/CHA type zeolite to remove methanol from a hydrocarbon stream. Other zeolites, such as a modified 4A type zeolite, AZ-300 (a spherical alumina-zeolite composite available from UOP), and OG-491 (a Type 3A alkali metal aluminosilicate available from UOP), have also been used. However, there are problems with these methods, including low capacity, co-adsorption, and high reactivity in the case of olefins. A number of different methods have been used for $CO_2$ removal from hydrocarbons. Adsorption with amines is widely used for $CO_2$ removal. Carbon molecular sieves have also been used separate $CO_2$ and $C_2H_4$ because of the difference in the diffusion/adsorption rates. However, carbon molecular sieves have a low static adsorption selectivity and low strength, and they cannot simultaneously remove moisture. Zeolites have not been used to separate $CO_2$ and $C_2H_4$ because similar molecular size and properties make it difficult to perform the separation.

Therefore, there is a need for improved methods of separating methanol and $CO_2$ from hydrocarbon stream.

DESCRIPTION

Figure 1:
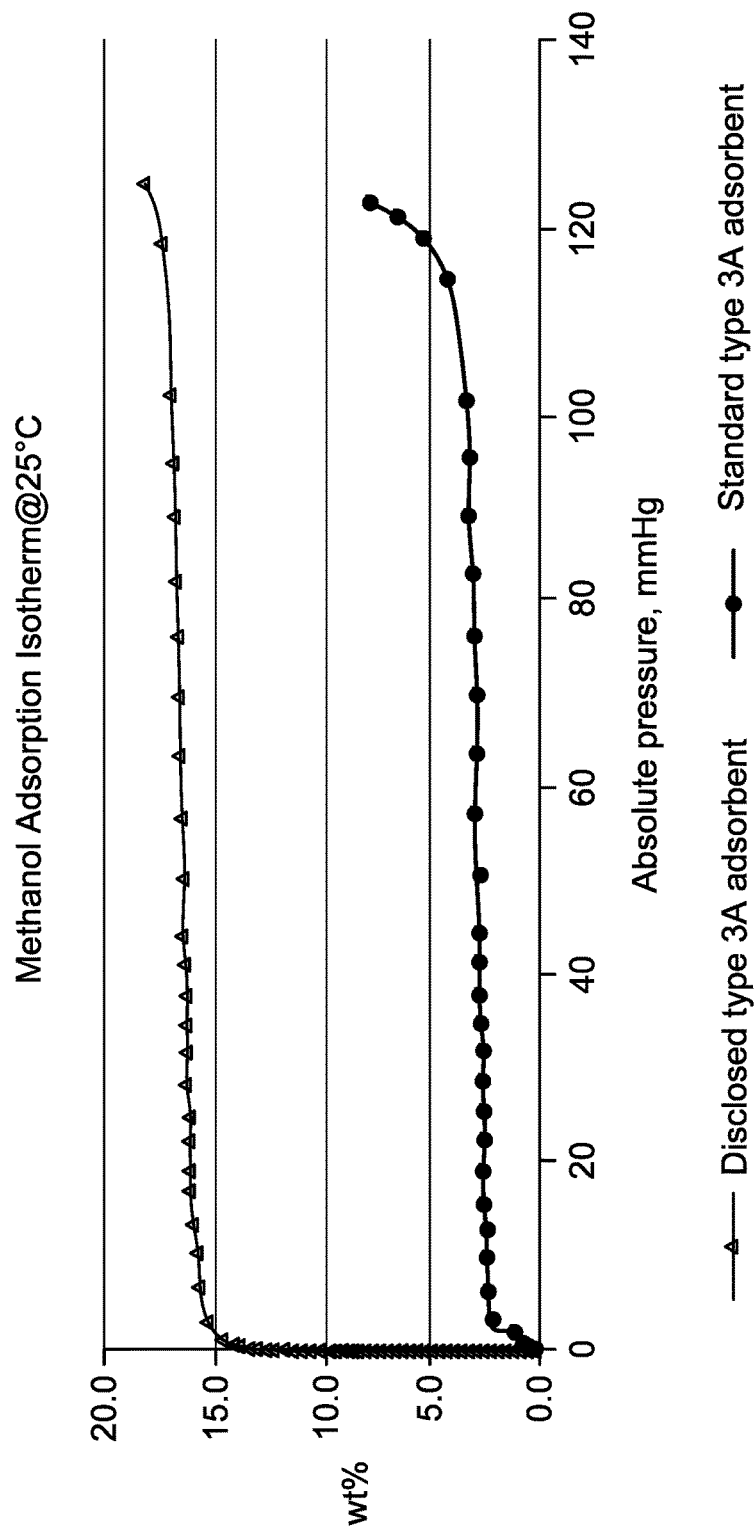
FIG. 1 is a graph comparing the methanol vapor adsorption isotherm of the 3A type zeolite adsorbent of the present invention and a commercial 3A type zeolite adsorbent.

The present invention meets that need by providing an adsorbent comprising a type 3A zeolite which can be used to remove methanol and $CO_2$ from hydrocarbon streams. The adsorbent has higher methanol removal capacity and low olefin co-adsorption capacity, as well as low reactivity in an olefin stream. This allows reduced adsorbent loading while maintaining downstream catalyst performance and product quality.

The adsorbent comprises a type 3A zeolite comprising less than 5% of a binder. An optional additive can be included. In that case, the total amount of the binder and the additive is less than 5%.

The adsorption process can obtain an outlet methanol content of 10 ppmw or less, or 7 ppmw or less, or 5 ppmw or less, or 3 ppmw or less, or 1 ppmw or less.

The adsorption process can obtain an outlet $CO_2$ content of 10 ppmv or less, or 8 ppmv or less, or 6 ppmv or less, or 4 ppmv or less, or 2 ppmv or less.

The 3A type zeolite is a potassium exchanged Linde Type A (LTA) zeolite which has a chemical formula of:

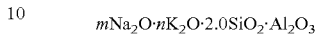

$m\text{Na}_2\text{O} \cdot n\text{K}_2\text{O} \cdot 2.0\text{SiO}_2 \cdot \text{Al}_2\text{O}_3$ where m+n=1. The pore opening is approximately 3 Å. Used as an adsorbent, zeolite-binder agglomerates as spheres or pellets which have high mechanical attrition resistance and strength are needed. The binder content is at least 10%, and in most cases it is above 15%. Considering the small pore opening size of 3A zeolite and molecular sieving properties of the zeolite, it was mainly used as a dehydration adsorbent. Here, a binderless 3A zeolite adsorbent was used in which the binder was converted to zeolite.

The 3A type zeolite can have K ion exchange ratio (K mol/(Kmol+Na mol)) of 30% to 70%. For example, at a 30% ion exchange ratio: m=0.7 and n=0.3, and at a 60% ion exchange ratio: m=0.4 and n=0.6. When potassium is at cationic exchangeable sites within the 3A zeolite adsorbent at 30% to 60%, the potassium ranges from about 8 wt. % to about 16 wt. % of the 3A zeolite adsorbent on a volatile-free basis.

In some embodiments, the type 3A zeolite may have one or more of the following characteristics: a porosity of 20% to 40% (ASTM 4284-17); and an ion exchange ratio of 30% to 60% (UOP 961-12 (available through ASTM International)). The porosity can be in the range of 15% to 50%, or 20% to 40%, or 20% to 35%. The ion exchange ratio can be in the range of 30% to 70%, or 30% to 60%, or 30% to 50%, or 35% to 70%, or 40% to 70%, or 40% to 60%.

In one embodiment, the adsorbent comprises a type 3A zeolite with less than 5% binder and a K ion exchange rate of 0.40-0.44 (K/K+Na). The elemental composition of the molecular sieve samples was analyzed using –X-ray fluorescence, inductively coupled plasma optical emission spectrometry (ICP-OES), or both. The adsorbent can be used to remove methanol from hydrocarbons, such as propene, and isobutylene. The adsorption selectivity of methanol/$C_3H_6$ at 1 mmHg and 298K is greater than 5000 mol/mol. The equilibrium adsorption capacities of methanol and $C_3H_6$ can be tested by physical adsorption isotherm using an accelerated surface area and porosimetry system at 298K, such as Micromeritics' 3Flex Surface Characterization Analyzer or BELSORP-max surface area and pore size distribution analyzer. The adsorption selectivity was defined as the adsorption capacity ratio of methanol/$C_3H_6$. The adsorbent can also be used to remove $CO_2$ from hydrocarbons, such as ethylene. The adsorbent has high $CO_2/C_2H_4$ selectivity. The adsorption selectivity of $CO_2/C_2H_4$ at 250 mm HG is about 23 mol/mol. The equilibrium adsorption capacities of $CO_2$, and $C_2H_4$ can be tested by physical adsorption isotherm using an accelerated surface area and porosimetry system at 298K, such as Micromeritics' 3Flex Surface Characterization Analyzer or BELSORP-max surface area and pore size distribution analyzer. The adsorption selectivity was defined as the adsorption capacity ratio of $CO_2/C_2H_4$. This is much higher than the typical selectivity of a carbon molecular sieve and other types of zeolite adsorbents. In addition, $CO_2$ has a smaller molecular size (kinetic diameter 3.3 Å) and higher affinity toward zeolite type adsorbents, both of which benefit $CO_2/C_2H_4$ separation.

The $CO_2$ capacity at 25° C. and 250 mm Hg is about 4-7%. The $C_2H_4$ capacity at 25° C. and 250 mm Hg is about 0.11%.

The adsorbent has a high water capacity. For example, the static water capacity may be in the range of 23-25%, while the dynamic water capacity may be greater than 18-20% at 25° C. and 17.5 mm Hg. A typical 3A type zeolite has a static water capacity greater than about 15-19%, while the dynamic water capacity is greater than about 13-14%.

The adsorbent can be made in the following manner. A binderless base 4A bead or pellet can be formed from a normal clay conversion process. A KCl solution can be used for ion exchange such that the K ion exchange ratio of the finished product is between 30% to 70%. The ion exchanged 3A type zeolite can be dried to remove moisture to the range of 8-25%. The dried adsorbent is then calcined at a temperature of 400-750° C. to obtain the finished adsorbent.

The adsorbent can be used in a purification unit which includes adsorption, desorption, and cooling. The adsorption is performed at a temperature typically in the range of 15-50° C. The regeneration of the adsorbent typically takes places at a temperature greater than 150° C. under a gas including, but not limited to, nitrogen, air, or methane.

Example

A 3A type zeolite was made from a binderless 4A type zeolite. The binderless 4A type zeolite was made by mixing adsorbent agglomerates comprised of 850 g Zeolite A and 150 g inert Kaolin binder. 30 g carboxymethyl cellulose (CMC) was added during the agglomerate-forming step which was formed into 8×12 mesh bead in an accretion bead forming equipment. The formed agglomerate was dried at 150° C. for 2 hr. The dried agglomerate was calcined by increasing the temperature at 5° C./min ramp to 675° C. and holding for 3 hr to convert the kaolin clay binder into meta-kaolin clay binder. The material was cooled down to 100° C. for packaging. The adsorbent was caustic digested at a temperature of about 88° C. using 1.8N sodium hydroxide solution for 20 hr to convert the meta-kaolin binder to binder-converted zeolite. The liquid was decanted, and deionized water at ambient temperature was used to wash the solid until the pH of the wash water was less than 11.

The binderless 4A zeolite adsorbent was exposed to 1N KCl solution at 45° C. and held for 8 hr for ion-exchange to produce the 3A type binderless zeolitic adsorbent.

The methanol adsorption capacity of the 3A type zeolite adsorbent was measured using physical adsorption isotherm and compared with several commercial adsorbents.

Table 1 shows the results of methanol adsorption capacity comparison.

TABLE 1

| | Methanol Adsorption Capacity | |
| --- | --- | --- |
| | 0.1 KPa | 1 KPa |
| Standard 3A Type Adsorbent | 0.81% | 2.3% |
| OG491 | 1-3% | n/a |
| AZ300 | 3-5% | n/a |
| Disclosed 3A adsorbent | 14.37% | 15.8% |

The 3A type zeolite adsorbent of the present invention has significantly higher methanol adsorption then the commercially available adsorbents.

FIG. 1 shows the methanol vapor adsorption isotherm comparison between the 3A type zeolite adsorbent of the present invention and a commercial 3A type zeolite adsorbent.

Figure 2:
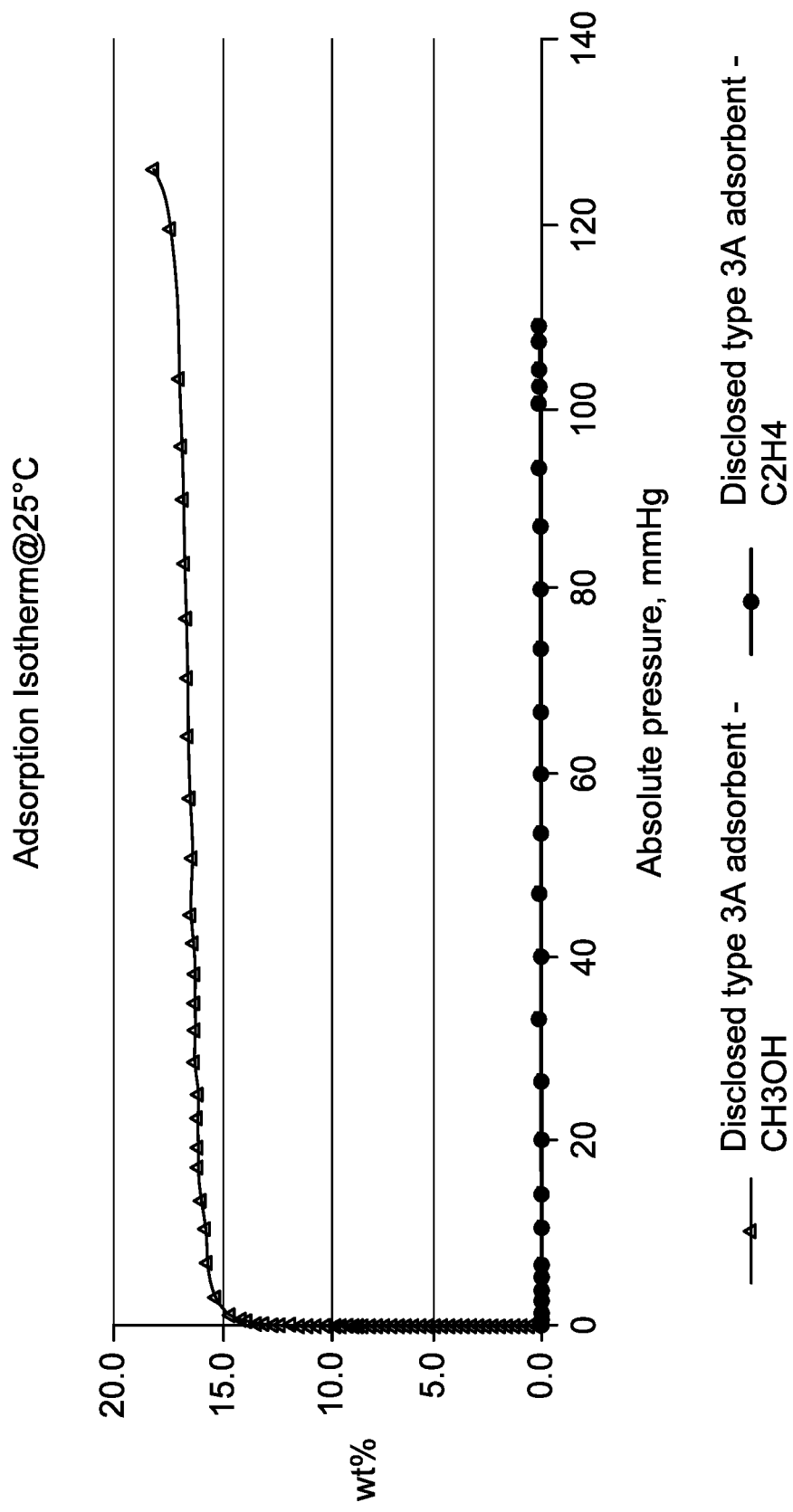
FIG. 2 is a graph showing the adsorption isotherm of the 3A type zeolite adsorbent of the present invention to methanol and ethylene.

FIG. 2 show the adsorption isotherm of 3A type zeolite adsorbent of the present invention to methanol and ethylene. It has high methanol adsorption capacity even at low partial pressure, e.g., 0.2 mm Hg, which can achieve 12 wt %. For ethylene, the adsorption capacity is only 0.15 wt % at 750 mm Hg.

Specific Embodiments

While the following is described in conjunction with specific embodiments, it will be understood that this description is intended to illustrate and not limit the scope of the preceding description and the appended claims.

A first embodiment of the invention is a process of removing methanol, $CO_2$ or both from a hydrocarbon stream, comprising contacting a hydrocarbon stream comprising hydrocarbon and the methanol, the $CO_2$, or both with an adsorbent comprising a 3A type zeolite to remove at least a portion of the methanol, the $CO_2$, or both to produce a purified hydrocarbon stream comprising 10.0 ppmw or less of methanol, or 10.0 ppmv or less of $CO_2$, or both, wherein the 3A type zeolite comprises less than 5% of a binder and has an ion exchange ratio of 30% to 70%. An embodiment of the invention is one, any or all of prior embodiments in this paragraph up through the first embodiment in this paragraph wherein the hydrocarbon comprises an olefin. An embodiment of the invention is one, any or all of prior embodiments in this paragraph up through the first embodiment in this paragraph wherein the olefin comprises ethylene or propene. An embodiment of the invention is one, any or all of prior embodiments in this paragraph up through the first embodiment in this paragraph wherein the 3A type zeolite has an ion exchange ratio of 30% to 50%. An embodiment of the invention is one, any or all of prior embodiments in this paragraph up through the first embodiment in this paragraph wherein the purified hydrocarbon stream comprises 1.0 ppmw or less of methanol. An embodiment of the invention is one, any or all of prior embodiments in this paragraph up through the first embodiment in this paragraph wherein the adsorbent has a porosity of 15% to 50%. An embodiment of the invention is one, any or all of prior embodiments in this paragraph up through the first embodiment in this paragraph wherein the adsorbent further comprises an additive. An embodiment of the invention is one, any or all of prior embodiments in this paragraph up through the first embodiment in this paragraph wherein a total amount of the binder and the additive is less than 5% wt. An embodiment of the invention is one, any or all of prior embodiments in this paragraph up through the first embodiment in this paragraph wherein the contacting takes place at a temperature in a range of 15° C. to 50° C. An embodiment of the invention is one, any or all of prior embodiments in this paragraph up through the first embodiment in this paragraph wherein the purified hydrocarbon stream comprising 2.0 ppmv or less of $CO_2$.

A second embodiment of the invention is a process of removing methanol, $CO_2$, or both from an ethylene or propene stream, comprising contacting the ethylene stream comprising ethylene or the propene stream comprising propene and the methanol, the $CO_2$, or both with an adsorbent comprising a 3A type zeolite to remove a portion of the methanol, the $CO_2$, or both to produce a purified ethylene or propene stream comprising 1.0 ppmw or less of methanol, or 10.0 ppmv or less of $CO_2$, or both, wherein the 3A type zeolite comprises less than 5% of a binder and has an ion exchange ratio of 30% to 70%. An embodiment of the invention is one, any or all of prior embodiments in this paragraph up through the second embodiment in this paragraph wherein the 3A type zeolite has an ion exchange ratio of 30% to 50%. An embodiment of the invention is one, any or all of prior embodiments in this paragraph up through the second embodiment in this paragraph wherein the purified ethylene or propene stream comprises 2.0 ppmv or less of $CO_2$. An embodiment of the invention is one, any or all of prior embodiments in this paragraph up through the second embodiment in this paragraph wherein the adsorbent has a porosity of 15% to 50%. An embodiment of the invention is one, any or all of prior embodiments in this paragraph up through the second embodiment in this paragraph wherein the adsorbent further comprises an additive. An embodiment of the invention is one, any or all of prior embodiments in this paragraph up through the second embodiment in this paragraph wherein a total amount of the binder and the additive is less than 5 wt. %. An embodiment of the invention is one, any or all of prior embodiments in this paragraph up through the second embodiment in this paragraph wherein the contacting takes place at a temperature in a range of 15° C. to 50° C.

A third embodiment of the invention is a composition comprising a 3A type zeolite comprising less than 5% of a binder, an ion exchange ratio of 30% to 60%, and a porosity of 15% to 50%. An embodiment of the invention is one, any or all of prior embodiments in this paragraph up through the third embodiment in this paragraph wherein the ion exchange ratio is 30% to 50%.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process of removing methanol, $CO_2$ or both from a hydrocarbon stream, comprising:
   contacting a hydrocarbon stream comprising hydrocarbon and the methanol, the $CO_2$, or both with an adsorbent comprising a 3A type zeolite to remove at least a portion of the methanol, the $CO_2$, or both to produce a purified hydrocarbon stream comprising 10.0 ppmv or less of methanol, and/or 10.0 ppmv or less of $CO_2$, wherein the 3A type zeolite comprises less than 5% of a binder and has an ion exchange ratio of 30% to 70%.

2. The process of claim 1 wherein the hydrocarbon comprises an olefin.

3. The process of claim 2 wherein the olefin comprises ethylene or propene.

4. The process of claim 1 wherein the 3A type zeolite has an ion exchange ratio of 30% to 50%.

5. The process of claim 1 wherein the purified hydrocarbon stream comprises 1.0 ppmv or less of methanol.

6. The process of claim 1 wherein the adsorbent has a porosity of 15% to 50%.

7. The process of claim 6 wherein a total amount of the binder and the additive is less than 5% wt.

8. The process of claim 1 wherein the adsorbent further comprises carboxymethylcellulose as an additive.

9. The process of claim 1 wherein the contacting takes place at a temperature in a range of 15° C. to 50° C.

10. The process of claim 1 wherein the purified hydrocarbon stream comprising 2.0 ppmv or less of $CO_2$.

11. The process of claim 1 wherein the 3A type zeolite is a potassium exchanged Linde Type A (LTA) zeolite which has a chemical formula of:

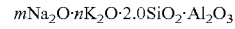

$$m\text{Na}_2\text{O} \cdot n\text{K}_2\text{O} \cdot 2.0\text{SiO}_2 \cdot \text{Al}_2\text{O}_3$$

where m+n=1.

12. A process of removing methanol, $CO_2$, or both from an ethylene or propene stream, comprising:
    contacting the ethylene stream comprising ethylene or the propene stream comprising propene and the methanol, the $CO_2$, or both with an adsorbent comprising a 3A type zeolite to remove a portion of the methanol, the $CO_2$, or both to produce a purified ethylene or propene stream comprising 1.0 ppmw or less of methanol, or 10.0 ppmv or less of $CO_2$, or both, wherein the 3A type zeolite comprises less than 5% of a binder and has an ion exchange ratio of 30% to 70%.

13. The process of claim 12 wherein the 3A type zeolite has an ion exchange ratio of 30% to 50%.

14. The process of claim 12 wherein the purified ethylene or propene stream comprises 2.0 ppmv or less of $CO_2$.

15. The process of claim 12 wherein the adsorbent has a porosity of 15% to 50%.

16. The process of claim 12 wherein the adsorbent further comprises carboxymethylcellulose as an additive.

17. The process of claim 16 wherein a total amount of the binder and the additive is less than 5 wt. %.

18. The process of claim 17 wherein the contacting takes place at a temperature in a range of 15° C. to 50° C.

* * * * *